US009198984B2

(12) United States Patent
Lock et al.

(10) Patent No.: US 9,198,984 B2
(45) Date of Patent: Dec. 1, 2015

(54) SCALABLE PRODUCTION METHOD FOR AAV

(75) Inventors: Martin Lock, Southampton, PA (US); Luc H Vandenberghe, Philadelphia, PA (US); James M. Wilson, Glen Mills, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 492 days.

(21) Appl. No.: 12/226,588

(22) PCT Filed: Apr. 27, 2007

(86) PCT No.: PCT/US2007/010055
§ 371 (c)(1),
(2), (4) Date: Oct. 21, 2008

(87) PCT Pub. No.: WO2007/127264
PCT Pub. Date: Nov. 8, 2007

(65) Prior Publication Data
US 2009/0275107 A1 Nov. 5, 2009

Related U.S. Application Data

(60) Provisional application No. 60/796,229, filed on Apr. 28, 2006.

(51) Int. Cl.
A61K 38/00 (2006.01)
C12N 7/00 (2006.01)
A61K 48/00 (2006.01)
C07K 14/005 (2006.01)

(52) U.S. Cl.
CPC ............ *A61K 48/0091* (2013.01); *C07K 14/005* (2013.01); *C12N 7/00* (2013.01); *C12N 2750/14151* (2013.01)

(58) Field of Classification Search
CPC ...................... C12N 15/86; C12N 2750/14122; C12N 2750/14145; C12N 2830/008; C12N 2750/14121; C12N 2799/025; C12N 15/8645; C12N 15/8613; C12N 2750/14132; C12N 2750/14162; C12N 2750/14171; C07K 14/005; C07K 16/081; G01N 33/56983
See application file for complete search history.

(56) References Cited

U.S. PATENT DOCUMENTS

| 6,759,237 | B1 | 7/2004 | Wilson |
| 7,105,345 | B2 | 9/2006 | Wilson |
| 7,186,552 | B2 | 3/2007 | Wilson |
| 7,282,199 | B2 | 10/2007 | Gao et al. |
| 2002/0127582 | A1* | 9/2002 | Atkinson et al. .................. 435/6 |
| 2006/0204479 | A1 | 9/2006 | Wilson |
| 2007/0036760 | A1 | 2/2007 | Wilson |
| 2008/0008684 | A1 | 1/2008 | Wilson |
| 2008/0050343 | A1 | 2/2008 | Wilson |
| 2008/0050345 | A1 | 2/2008 | Wilson |
| 2008/0075737 | A1 | 3/2008 | Gao |
| 2008/0075740 | A1 | 3/2008 | Gao |

FOREIGN PATENT DOCUMENTS

| EP | 1 486 567 A | 12/2004 |
| EP | 1 127 150 | 5/2007 |
| WO | WO 00/28061 | 5/2000 |
| WO | WO 03/052051 A2 | 6/2003 |
| WO | WO 2005/005610 A | 1/2005 |
| WO | WO 2005/033321 | 4/2005 |
| WO | WO 2006/110689 A2 | 10/2006 |
| WO | WO 2008/027084 | 3/2008 |

OTHER PUBLICATIONS

Sommer et al., Quantification of Adeno-Associated Virus Particles and Empty Capsids by Optical Density Measurement, 2003, Molecular Therapy, vol. 7, No. 1, pp. 122-128.*
Okada et al., 421. Large-Scale Production of AAV and Adenovirus Vectors Using Active Gassing with Large Culture Vessel, 2004, Molecular Therapy, vol. 9, Supplement 1, pp. S161-S162.*
Jenny et al., Evaluation of a serum-free medium for the production of rAAV-2 using HeLa derived producer cells, 2005, Cytotechnology, vol. 49, pp. 11-23.*
Gao et al, Clades of Adeno-Associated Viruses are Widely disseminated in Human Tissues, J. Virology, 78(12):6381-6388, (Jun. 2004).
Halbert et al, Adeno-Associated Virus Type 6 (AAV6) Vectors Mediate Efficient Transduction of Airway Epithelial Cells in Mouse Lungs Compared to that of AAV2 Vectors, J. Virol., 75(14):6615-6624, (Jul. 2001).
Walsh et al, Parvovirus-Mediated Gene Transfer for the Haemophilias, Haemophilia, 8, Suppl. 2) p. 60-67, (Mar. 2002).
Müller et al, Cardiovascular Research, Improved Cardiac Gene Trasnfer by Transcriptional and Transductional Targeting of Adeno-Associated Viral Vectors, 70(1):70-8, E-published (Jan. 31, 2006), (Apr. 2006).
Kern et al, Identification of a Heparin-Binding Motif on Adeno-Associated Virus Type 2 Capsids, Journal of Virology, vol. 77, No. 20, pp. 11072-11081, (Oct. 2003).

(Continued)

*Primary Examiner* — Benjamin P Blumel
(74) *Attorney, Agent, or Firm* — Howson & Howson LLP

(57) ABSTRACT

A method for producing AAV, without requiring cell lysis, is described. The method involves harvesting AAV from the supernatant. For AAV having capsids with a heparin binding site, the method involves modifying the AAV capsids and/or the culture conditions to ablate the binding between the AAV heparin binding site and the cells, thereby allowing the AAV to pass into the supernatant, i.e., media. Thus, the method of the invention provides supernatant containing high yields of AAV which have a higher degree of purity from cell membranes and intracellular materials, as compared to AAV produced using methods using a cell lysis step.

16 Claims, 6 Drawing Sheets

(56) References Cited

OTHER PUBLICATIONS

Opie et al, Identification of Amino Acid Residues in the Capsid Proteins of Adeno-Associated Virus Type 2 that Contribute to Heparan Sulfate Proteoglycan Binding, Journal of Virology, vol. 77, No. 12, pp. 6995-7006, (Jun. 2003).

Lochrie et al, Mutations on the External Surfaces of Adeno-Associated Virus Type 2 Capsids that affect Transduction and Neutralization, Journal of Virology, vol. 80, No. 2, pp. 821-834, (Jan. 2006).

Wu et al, Single Amino Acid changes can Influence Titer, Heparin Binding, and Tissue Tropism in Different Adeno-Associated Virus Serotypes, Journal of virology, vol. 80, No. 22, pp. 11393-11397, (Nov. 2006).

Vandenberghe et al, Heparin Binding Directs Activation of T Cells Against Adeno-Associated Virus Serotype 2 Capsid, Nature Medicine, vol. 12, No. 8, pp. 967-971, (Aug. 2006).

Vandenberghe et al, Efficient Serotype-Dependent Release of Functional Vector into the Culture Medium During Adeno-Associated Virus Manufacturing, Human Gene Therapy, 21(10):1251-1257, (Oct. 2010).

Communication dated May 31, 2010 from corresponding EP Application No. 07 756 027.4-2401 and Response dated Dec. 10, 2010.

Notice on the First Office Action issued by The State Intellectual Property Office the People's Republic of China, dated Mar. 7, 2012, issued in Application No. 200780014975.8.

Feudner et al, Optimization of recombinant adeno-associated virus production using an herpes simplex virus aplicon system, Journal of Virological Methods (Aug. 2001) vol. 96 No. 2, pp. 97-105.

Communication dated Jun. 12, 2012 issued in Japanese Patent Application No. 507783/09.

\* cited by examiner

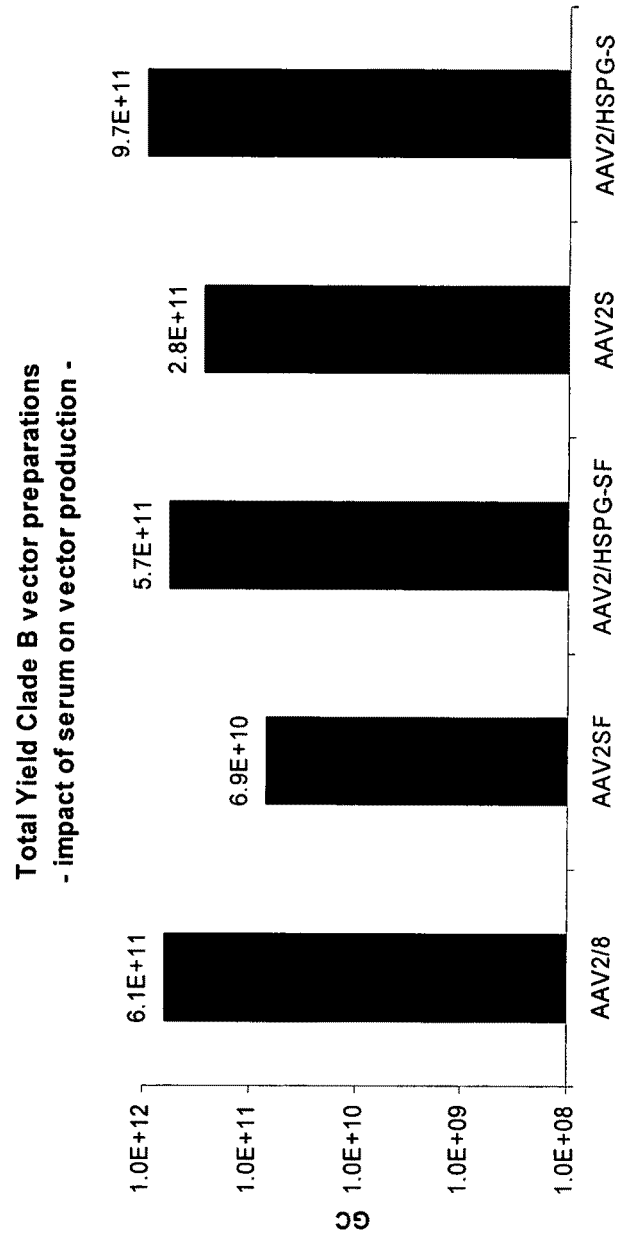

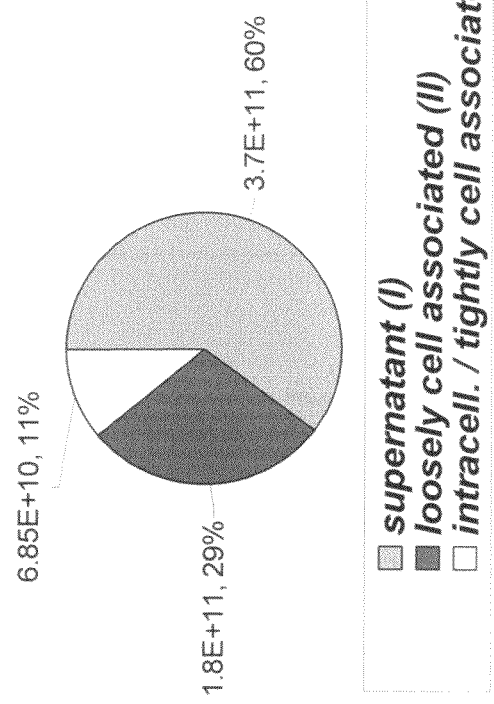

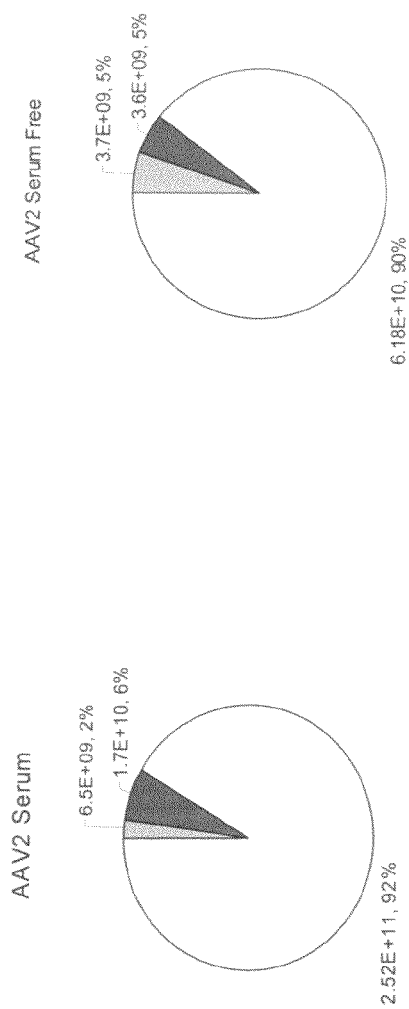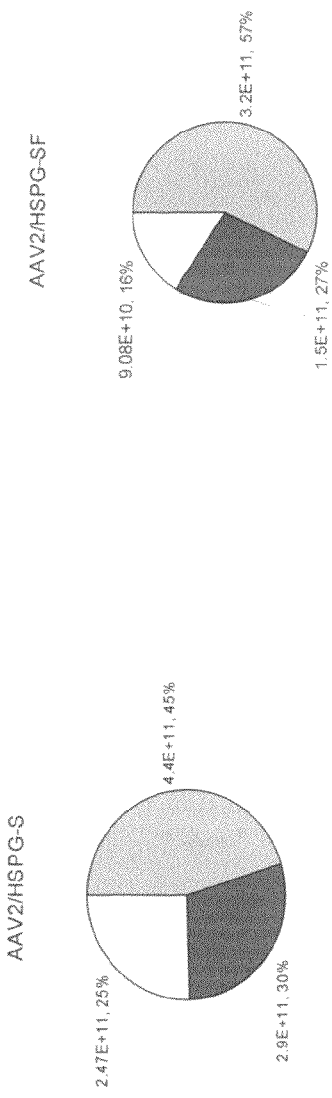

SCALABLE PRODUCTION METHOD FOR AAV

CROSS-REFERENCE TO RELATED APPLICATIONS

This is a national stage application under 35 U.S.C. 371 of PCT/US2007/010055, filed on Apr. 27, 2007 which claims the benefit under 35 U.S.C. 119(e) of U.S. Patent Application No. 60/796,229, filed Apr. 28, 2006.

STATEMENT REGARDING FEDERALLY SPONSORED RESEARCH OR DEVELOPMENT

This application describes work supported at least in part by a grant from the National Institutes of Health, NHLBI grant number P01-HL-059407. The US government may have certain rights in this invention.

BACKGROUND OF THE INVENTION

This invention describes a novel way to harvest and produce AAV.

Adeno-associated virus (AAV), a member of the Parvovirus family, is a small nonenveloped, icosahedral virus with a single-stranded linear DNA genome of 4.7 kilobases (kb) to 6 kb. AAV is assigned to the genus, Dependovirus, because the virus was discovered as a contaminant in purified adenovirus stocks. AAV's life cycle includes a latent phase at which AAV genomes, after infection, are integrated into host genomes and an infectious phase in which, following either adenovirus or herpes simplex virus infection, the integrated AAV genomes are subsequently rescued, replicated, and packaged into infectious viruses. The properties of non-pathogenicity, broad host range of infectivity, including non-dividing cells, and integration make AAV an attractive delivery vehicle.

A variety of different AAV sequences and methods for isolating same from tissues have been described. AAV1-6, AAV7, AAV9 and AAV9, amongst other AAV sequences obtained from simian or human tissue sources have been described. See, e.g., International Patent Publication Nos. WO 02/33269, WO 02/386122 (AAV8), and International Patent Publication No. WO 2005/033321. With this, a move away from defining AAV strictly by serologic cross-reactivity (serotypes) has occurred. Recent literature defines the relationship between these AAV in terms of phylogenetic relatedness, proposing groups termed "clades". See, e.g., Gao et al, J Virol, 78(12):6381-6388 (June 2004); International Patent Publication No. WO 2005/033321.

Current methodology for production of AAV has been founded largely in view of the observation that AAV2 is cell-associated and thus, thought to reside primarily in the producing cells. Therefore most current state-of-the-art AAV production strategies obtain vector particles from the cellular pellet of the production cell line. Each of these strategies employs some methodology of releasing vector from the cell pellet by sonication, enzymatic, chemical or physical lysis. This unfortunately releases all intracellular proteins and debris into the viral harvest. Therefore the subsequent purification procedure is more demanding. Because of the relatively low efficiency of both production and purification, it is necessary to start with a large amount of producing cells.

What are needed are efficient methods of production and purification of AAV.

SUMMARY OF THE INVENTION

The present invention provides a method for producing AAV, without requiring the termination of the virus-producing cell culture. The method involves harvesting AAV released into the supernatant without requiring collection of a cell pellet or cell disruption. In one embodiment, the method involves modifying the AAV capsids, the cells, and/or the culture conditions to substantially reduce or eliminate binding between the AAV heparin binding site and the producer cells, thereby allowing the AAV to pass into the supernatant, i.e., media. Thus, the method of the invention provides supernatant containing high yields of AAV which have a higher degree of purity from cell membranes and intracellular materials, as compared to AAV produced using methods using a cell collection and/or cell lysis step.

This technology can be applied for efficient and scalable AAV production with significant improvements in financial and time cost. This technology allows small scale AAV production and its commercial application for an all-inclusive kit for research purposes. Since AAV can be harvested multiple times from the supernatant, a continuous system or bioreactor allows production of particle amounts necessary for clinical use or wide pharmaceutical application without cellular substrate being the limitation for production. Optionally in combination with the use of a growth medium that is absent or low in serum or proteins, purification is significantly simplified. This technology can be applied in combination with more efficient methods of purification and concentration than could be used with the prior art production methods and/or in the presence of significant amounts of intracellular material.

Still other advantages of the present invention will be apparent from the detailed description of the invention.

BRIEF DESCRIPTION OF THE DRAWINGS

FIG. 1 illustrates the effect of a heparan sulfate glycoprotein (HSPG) on production of AAV2 and AAV2HSPG- in the presence (S) or absence of serum (SF) with AAV2/8 production as positive control.

FIG. 2A shows quantification of DNase-resistant AAV particles (drp) in supernatant (I), loosely cell associated (II) and tightly cell associated (III) fraction for AAV2/8 positive control.

FIGS. 2B-2E show similar fractions for AAV2 and AAV2HSPG- in the presence (Serum or S) or absence (Serum Free or SF) of serum.

DETAILED DESCRIPTION OF THE INVENTION

Figure 3:
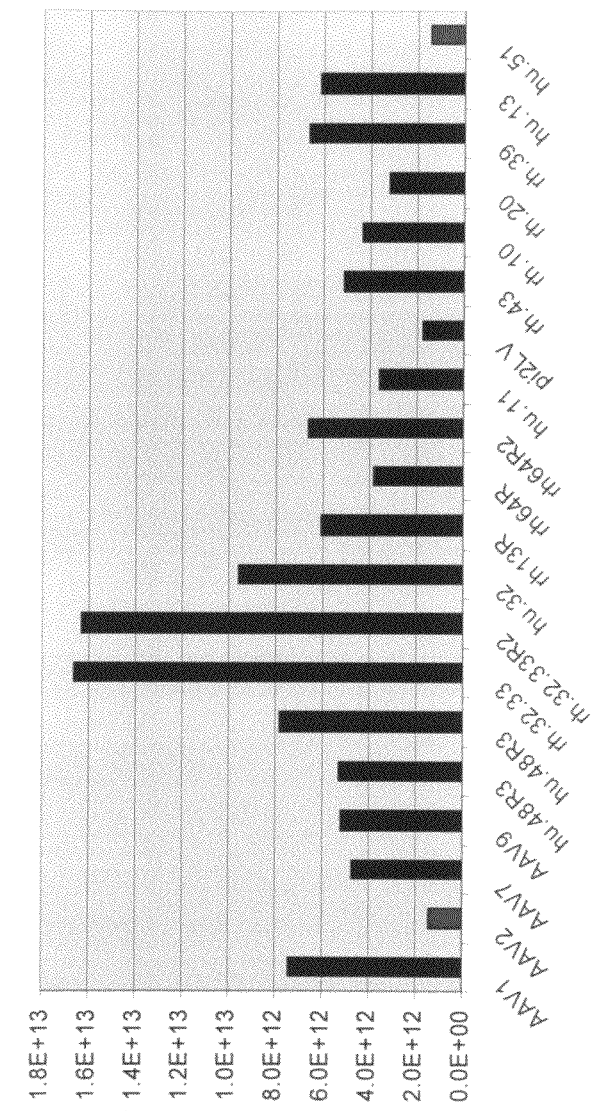
FIG. 3 illustrates the yield of AAV isolates from a single 15 cm dish transfection. All non-heparin binding isolates yield higher than $2\times10^{12}$ GC ranging up to $1\times10^{13}$ GC total. AAV2 and isolate hu.51 has been shown to bind heparin and is limited in production.

The present invention provides a method for producing AAV, without requiring cell disruption. The method involves harvesting AAV from the supernatant of a viral production culture.

For those AAVs that do not show affinity with heparansulfate proteoglycan or heparin, which comprises the majority of AAV species, a large fraction of DNase resistant, infectious particles is located in the culture supernatant or is only loosely cell-associated. This is observed without induced viral, osmolytic or any other type of lysis.

This invention allows a scalable technology for production of AAV for use in a variety of gene transfer and/or vaccine applications. It also dramatically reduces the stringency of purification when used in combination with low- or non-protein contaminating media for harvest. This production method can be applied in combination with suitable methods for purification and concentration including, e.g., chromatography, filtration or precipitation for purification and concentration.

Since most current AAV production strategies use the cell pellet as a substrate for isolating particles, such methods are by definition an iterative process that excludes a continuous harvesting strategy.

In contrast to current methodologies, in one embodiment, the present invention provides a method in which the supernatant is the major source for many AAVs. This allows repetitive or continuous harvesting of the same producer cells for production of larger amounts of AAV for clinical or pre-clinical research or therapy. In the current cell pellet harvest and subsequent purification methods, large amounts of particles are needed to efficiently provide a usable viral titer. Therefore there is a threshold below which recovery of a usable amount of particles is technically not feasible. In one embodiment, an AAV vector secretes at least about 10% Dnase-resistant vector particles or genomes (drp vg) from the cells in which it is produced. Such drp vg represent genomic sequences (e.g., a minigene, cassette, and/or AAV nucleic acid sequences) packaged in AAV capsid. In other embodiments, an AAV vector secretes at least about 20% drp vg. In still other embodiments, an AAV vector secretes at least about 40% drp vg. By the more efficient production strategy provided herein, scalability is possible for both small and large particle needs. Therefore viral production can be customized depending on expected quantities required, without the requirement for cell lysis or discontinuing the cell culture.

For example, AAV8 vectors have been found to secrete, on average, more than 40% of their viral particles into the supernatant in a 293 cell-based triple transfection production method. Other vectors based on AAV7 and rh8R have been found to secrete in this same range. Still other vectors have been found to secrete, on average, more than 30% of the viral particles in the supernatant in this system, e.g., AAV1 [capsid protein provided in SEQ ID NO: 2], AAV6 [AAV6 capsid protein provided in SEQ ID NO: 3], AAV6.1 [SEQ ID NO: 3, with a K531E change in the capsid protein], AAV6.1.2 [SEQ ID NO: 3, with K531E, F129L], rh.32.33 [capsid protein provided in SEQ ID NO: 4], rh.10 [capsid protein provided in SEQ ID NO: 5], and rh64R1 [rh64 capsid protein provided in SEQ ID NO: 6, with a R697W] and rh8R [rh8 capsid protein provided in SEQ ID NO: 7, with D531E]. In yet another example, other AAV vectors have been found to secrete on average more than 20% of their viral particles into the supernatant during production following triple transfection in this system. Still other AAV vectors, e.g., those based on AAV9 [capsid protein provided in SEQ ID NO: 8], have been found to release more than 10% of their viral particles into the supernatant in this system. Yet other examples include AAVs which secrete more than 10% of their viral particles into the supernatant are used in the methods of the invention. In one embodiment, these vectors produced in this matter are from AAVs which naturally secrete out of the cell in which they are produced.

In another embodiment, the AAVs are modified to permit their secretion. In one embodiment, the inventors have found that an AAV having a heparin binding domain and which is characterized by having transduction (infectious) ability blocked by heparin, do not secrete in detectable amounts. Examples of such AAV are AAV2 [capsid protein provided in SEQ ID NO: 9], which is mostly cell associated during production, and AAV3 [capsid protein provided in SEQ ID NO: 10]. Thus, in one embodiment, the method involves modifying the AAV capsids, the cells, and/or the culture conditions to substantially reduce or eliminate binding between the AAV heparin binding site and the producer cells, thereby allowing the AAV to pass into the supernatant, i.e., media.

The method of the invention provides supernatant containing high yields of AAV which have a higher degree of purity from cell membranes, proteins, and intracellular materials, as compared to AAV recovered following cell lysis. In one embodiment, this invention in contrast starts from supernatant without lysis and thereby simplifies any subsequent purification. Limited amount of cell debris is found in the supernatant in normal culture and amounts to a dramatic reduction of protein contamination. In one embodiment, serum-free medium is utilized to avoid the contaminating effect of the serum or other proteins introduced by the growth medium.

In one aspect, the present invention provides a method of producing an AAV in a viral production culture. The sequences of a variety of AAV have been previously described. See, e.g., AAV 1 (U.S. Pat. No. 6,759,237), AAV2, AAV3, AAV4, AAV5, AAV6, AAV7, AAV8, AAV9, rh32.33, rh.10, hu.11, others AAV from human and non-human sources, see, e.g., International Patent Publication Nos. WO 02/33269, WO 02/386122 (AAV8), and GenBank, and such sequences as have been altered to correct singleton errors, e.g., AAV6.2, AAV6.1, AAV6.1.2, rh64R1 and rh8R [see, e.g., WO 2006/110689, published Oct. 19, 2006]. Alternatively, other AAV sequences including those identified by one of skill in the art using known techniques [See, e.g., International Patent Publication No. WO 2005/033321 and GenBank] or by other means may be modified as described herein.

Certain AAV sequences are natively devoid of such a heparin binding site. For AAV lacking a heparin binding site, e.g., AAV8 [capsid protein provided in SEQ ID NO: 11], no modification of the AAV sequence, cell or media is required. The ability of an AAV capsid to bind heparin can be readily identified using a variety of assay formats and heparin or portions thereof for binding an AAV. Further, the ability of heparin to block the infectious/transduction ability of an AAV can readily be determined by one of skill in the art. A suitable assay for determining the ability of heparin to block any infection/transduction of transduction of an AAV has been described, e.g., in C. Halbert et al, *J Virol,* 75(14):6615-6624 (July 2001) and C. E. Walsh and H. Chao, *Haemophilia,* 8 (Suppl. 2), p. 60-67 (2002).

Other AAV sequences, e.g., AAV6, have a heparin binding site, but the ability of AAV6 to infect is partially inhibited, not blocked, by the presence of heparin. The AAV6 vp1 capsid sequence has been described as having a single amino acid residue that mediates heparin binding, the native lysine reside at position 531 [SEQ ID NO: 3]. [The sequence of AAV6 is provided in International Patent Appln No. PCT/US06/13375 and the residue number is based on the numbering scheme provided in that international application (see, e.g., Table)]. In such a case, no modification of this AAV sequence is required since it has been found to be only loosely cell associated.

In one embodiment, for AAV having a heparin binding site and which has its ability to infect/transfect cells blocked by heparin, the invention provides for modification of the AAV to reduce or eliminate heparin-binding in order to increase the amount of viral particles secreted into the supernatant. In one embodiment, a heparin binding domain is an Arg-Xaa-Xaa-Arg (RxxR) [SEQ ID NO: 12] motif as has been described in AAV2 (i.e., about amino acids 585 to 588 of the AAV2 vp1 capsid protein, SEQ ID NO: 9, Kern, et al., *J Virol* 77:11072-81; Opie, et al., *J Virol* 77:6995-7006 (based upon the numbering illustrated in WO 02/33269)]. Xaa represents any amino acid. The inventors have identified other AAV capsids having RxxR motifs, several of which are Clade B AAVs. Examples of such AAV capsids having RxxR motifs include, hu.51 [SEQ ID NO: 13], hu.34 [SEQ ID NO: 14], hu.35 [SEQ ID NO: 15], hu.45 [SEQ ID NO: 16], and hu.47 [SEQ ID NO: 17]. Other AAV having an RxxR domain can be readily identified by one of skill in the art from among those AAV sequences which have been described. In addition, other heparin binding sites can be readily identified in AAV using techniques known to those of skill in the art. In another example, AAV3 binds heparin; however, it does not contain the RxxR domain.

The inventors have found that by changing an amino acid residue(s) of a heparin binding sequence to contain a non-conservative amino acid change, not only is heparin binding ablated, but also, T cell activation is significantly reduced. This is the subject of the co-owned application, "Modified AAV Vectors Having Reduced Capsid Immunogenicity and Use Thereof", which claims priority of U.S. provisional Patent Application No. 60/795,965, filed Apr. 28, 2006, which is hereby incorporated by reference.

In one embodiment, the invention provides a method for producing an AAV in a viral culture, wherein the AAV is modified to ablate the heparin binding domain.

In one embodiment, the nucleic acid sequence encoding the AAV capsid heparin binding site is modified using site-specific mutagenesis techniques, in which the codon for the amino acid residue(s) responsible for mediating heparin binding is altered to make a non-conservative change in the encoded amino acid. Examples of non-conservative amino acid changes include those, e.g., substitution of one amino acid with another amino acid of different chemical structure (properties), which affect protein function. The following table illustrates the most common amino acids and their properties.

| Amino acid | Abbrev. | Hydro-phobic | Polar | Charged | Aromatic or Aliphatic | Codon |
|---|---|---|---|---|---|---|
| Alanine | Ala, A | X | — | — | — | GCU, GCC, GCA, GCG |
| Cysteine | Cys, C | X | — | — | — | UGU, UGC |
| Aspartate | Asp, D | — | X | negative | — | GAU, GAC |
| Glutamate | Glu, E | — | X | negative | — | GAA, GAG |
| Phenylalanine | Phe, F | X | — | — | Aromatic | UUU, UUC |
| Glycine | Gly, G | X | — | — | — | GGU, GGC, GGA, GGG |
| Histidine | His, H | — | X | positive | Aromatic | CAU, CAC |
| Isoleucine | Ile, I | X | — | — | Aliphatic | AUU, AUC, AUA |
| Lysine | Lys, K | — | X | positive | — | AAA, AAG |
| Leucine | Leu, L | X | — | — | Aliphatic | UUA, UUG, CUU, CUC, CUA, CUG |
| Methionine | Met, M | X | — | — | — | AUG |
| Asparagine | Asn, N | — | X | — | — | AAU, AAC |
| Proline | Pro, P | X | — | — | — | CCU, CCC, CCA, CCG |
| Glutamine | Gln, Q | — | X | — | — | CAA, CAG |
| Arginine | Arg, R | — | X | positive | — | CGU, CGC, CGA, CGG, AGA, AGG |
| Serine | Ser, S | — | X | — | — | UCU, UCC, UCA, UCG, AGU, AGC |
| Threonine | Thr, T | X | X | — | — | ACU, ACC, ACA, ACG |
| Valine | Val, V | X | — | — | Aliphatic | GUU, GUC, GUA, GUG |
| Tryptophan | Trp, W | X | — | — | Aromatic | UGG |
| Tyrosine | Tyr, Y | X | X | — | Aromatic | UAU, UAC |

For example, the nucleic acid sequence encoding the heparin binding site is modified using site-specific mutagenesis techniques. For example in an RxxR motif [SEQ ID NO: 3], the codon for the initial arginine and/or the last arginine of the motif is altered to change one (or both) of the amino acids to a non-conservative amino acid. It has been found that altering either one of the arginines in this motif prevents heparin binding. As illustrated herein, where the heparin binding motif is RxxR, the first amino acid of the modified heparin sulfate glycoprotein binding site can be changed from Arg to Ser or Glu. In another embodiment, the last amino acid of the modified heparin sulfate glycoprotein binding site is changed from Arg to Thr. In another embodiment, the lysine at position 531 of the AAV6 vp1 capsid protein [SEQ ID NO: 3] is changed to a non-conservative amino acid. Non-conservative amino acid changes other than those illustrated herein may be selected by one of skill in the art.

Similarly, other heparin binding domains may be identified using techniques known to those of skill in the art and modified using site-specific mutagenesis or another suitable technique for altering the coding sequence for the arginine. See, e.g., Sambrook et al, Molecular Cloning: A Laboratory Manual, Cold Spring Harbor Press (Cold Spring Harbor, N.Y.).

Additionally, other methods of altering the sequence of a heparin binding domain may be utilized to prevent heparin binding. In another embodiment, binding of heparin to an AAV containing a heparin binding site is ablated by methods other than altering the sequence of the heparin binding site. For example, one may provide the AAV capsid with a molecule which effectively masks the heparin binding site in the producer cell.

In yet another embodiment, one may modify the producer cell to eliminate or substantially reduce heparin production, e.g., using RNA targeted to or mutating genes important for heparin biogenesis, either transiently or permanently. In another embodiment, a producer cell line naturally defective in heparin biogenesis might be used.

A viral cell culture utilizes cells containing, either stably or transiently, at least the minimum components required to generate an AAV particle, where production of an AAV DNase resistant genome containing particles involves packaging an expression cassette into an AAV capsid. The minimum required components include, an expression cassette to be packaged into the AAV capsid, an AAV cap, and an AAV rep or a functional fragment thereof, and helper functions.

A variety of suitable cells and cell lines have been described for use in production of AAV. The cell itself may be selected from any biological organism, including prokaryotic (e.g., bacterial) cells, and eukaryotic cells, including, insect cells, yeast cells and mammalian cells. Particularly desirable host cells are selected from among any mammalian species, including, without limitation, cells such as A549, WEHI, 3T3, 10T1/2, BHK, MDCK, COS 1, COS 7, BSC 1, BSC 40, BMT 10, VERO, WI38, HeLa, a HEK 293 cell (which express functional adenoviral E1), Saos, C2C12, L cells, HT1080, HepG2 and primary fibroblast, hepatocyte and myoblast cells derived from mammals including human, monkey, mouse, rat, rabbit, and hamster. The selection of the mammalian species providing the cells is not a limitation of this invention; nor is the type of mammalian cell, i.e., fibroblast, hepatocyte, tumor cell, etc.

AAV sequences may be obtained from a variety of sources. For example, a suitable AAV sequence may be obtained as described in WO 2005/033321 or from known sources, e.g., the American Type Culture Collection, or a variety of academic vector core facilities. Alternatively, suitable sequences are synthetically generated using known techniques with reference to published sequences. Examples of suitable AAV sequences are provided herein.

Generally, the expression cassette is composed of, at a minimum, a 5' AAV inverted terminal repeat (ITR), a nucleic acid sequence encoding a desirable therapeutic, immunogen, or antigen operably linked to regulatory sequences which direct expression thereof, and a 3' AAV ITR. In one embodiment, the 5' and/or 3' ITRs of AAV serotype 2 are used. However, 5' and 3' ITRs from other suitable sources may be selected. It is this expression cassette that is packaged into a capsid protein to form an AAV virion (particle).

In addition to the expression cassette, the cell contains the sequences which drive expression of an AAV capsid in the cell (cap sequences) and rep sequences of the same source as the source of the AAV ITRs found in the expression cassette, or a cross-complementing source. The AAV cap and rep sequences may be independently selected from different AAV parental sequences and be introduced into the host cell in a suitable manner known to one in the art. While the full-length rep gene may be utilized, it has been found that smaller fragments thereof, i.e., the rep78/68 and the rep52/40 are sufficient to permit replication and packaging of the AAV.

The cell also requires helper functions in order to package the AAV of the invention. Optionally, these helper functions may be supplied by a herpesvirus. In another embodiment, the necessary helper functions are each provided from a human or non-human primate adenovirus source, such as are available from a variety of sources, including the American Type Culture Collection (ATCC), Manassas, Va. (US). The sequences of a variety of suitable adenoviruses have been described. See, e.g., chimpanzee adenovirus C1 and C68 [U.S. Pat. No. 6,083,716]; Pan 5, Pan6 and Pan7, [WO 02/33645], hybrid adenoviruses such as those described [e.g., WO 05/001103], and GenBank.

In one embodiment, the host cell contains at least the minimum adenovirus DNA sequences necessary to express an E1a gene product, an E1b gene product, an E2a gene product, and/or an E4 ORF6 gene product. The host cell may contain other adenoviral genes such as VAI RNA, but these genes are not required. In one embodiment, the cell used does not carry any adenovirus gene other than E1, E2a and/or E4 ORF6; does not contain any other virus gene which could result in homologous recombination of a contaminating virus during the production of rAAV; and it is capable of infection or transfection by DNA and expresses the transfected gene(s).

One cell useful in the present invention is a host cell stably transformed with the sequences encoding rep and cap, and which is transfected with the adenovirus E1, E2a, and E4ORF6 DNA and a construct carrying the expression cassette as described above. Stable rep and/or cap expressing cell lines, such as B-50 (International Patent Application Publication No. WO 99/15685), or those described in U.S. Pat. No. 5,658,785, may also be similarly employed. Another desirable host cell contains the minimum adenoviral DNA which is sufficient to express E4 ORF6. Yet other cell lines can be constructed using the novel modified cap sequences of the invention.

The preparation of a host cell according to this invention involves techniques such as assembly of selected DNA sequences. This assembly may be accomplished utilizing conventional techniques. Such techniques include cDNA and genomic cloning, which are well known and are described in Sambrook et al., Molecular Cloning: A Laboratory Manual, Cold Spring Harbor Press, Cold Spring Harbor, N.Y., including polymerase chain reaction, synthetic methods, and any other suitable methods which provide the desired nucleotide sequence.

The required components for AAV production (e.g., adenovirus E1a, E1b, E2a, and/or E4ORF6 gene products, rep or a fragment(s) thereof, cap, the expression cassette, as well as any other desired helper functions), may be delivered to the packaging host cell separately, or in combination, in the form of any genetic element which transfer the sequences carried thereon.

As used herein, a genetic element (vector) includes, e.g., naked DNA, a plasmid, phage, transposon, cosmid, episome, a protein in a non-viral delivery vehicle (e.g., a lipid-based carrier), virus, etc., which transfers the sequences carried thereon. The selected vector may be delivered by any suitable method, including transfection, electroporation, liposome delivery, membrane fusion techniques, high velocity DNA-coated pellets, viral infection and protoplast fusion. The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. See, e.g., K. Fisher et al, *J. Virol.*, 70:520-532 (1993) and U.S. Pat. No. 5,478,745.

In one embodiment, one or more of the adenoviral genes are stably integrated into the genome of the host cell or stably expressed as episomes. The promoters for each of the adenoviral genes may be selected independently from a constitutive promoter, an inducible promoter or a native adenoviral promoter. The promoters, for example, may be regulated by a specific physiological state of the organism or cell (i.e., by the differentiation state or in replicating or quiescent cells) or by exogenously added factors.

In one embodiment, a stable host cell will contain the required component(s) under the control of a regulatable promoter. However, the required component(s) may be under the control of a constitutive promoter.

Regulatable promoters allow control of gene expression by exogenously supplied compounds, environmental factors such as temperature, or the presence of a specific physiological state, e.g., acute phase, a particular differentiation state of the cell, or in replicating cells only. Regulatable promoters and systems are available from a variety of commercial sources, including, without limitation, Invitrogen, Clontech and Ariad. Many other systems have been described and can be readily selected by one of skill in the art. Examples of promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system [WO 98/10088]; the ecdysone insect promoter [No et al, *Proc. Natl. Acad. Sci. USA*, 93:3346-3351 (1996)], the tetracycline-repressible system [Gossen et al, *Proc. Natl. Acad. Sci. USA*, 89:5547-5551 (1992)], the tetracycline-inducible system [Gossen et al, *Science*, 268:1766-1769 (1995), see also Harvey et al, *Curr. Opin. Chem. Biol.*, 2:512-518 (1998)], the RU486-inducible system [Wang et al, *Nat. Biotech.*, 15:239-243 (1997) and Wang et al, *Gene Ther.*, 4:432-441 (1997)] and the rapamycin-inducible system [Magari et al, *J. Clin. Invest.*, 100:2865-2872 (1997)]. Still other types of inducible promoters which may be useful in this context are those which are regulated by a specific physiological state, e.g., temperature, acute phase, a particular differentiation state of the cell, or in replicating cells only.

In another embodiment, the native promoter is used. The native promoter may be used when it is desired that expression of the gene product should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

Another embodiment of the transgene includes a transgene operably linked to a tissue-specific promoter. For instance, if expression in skeletal muscle is desired, a promoter active in muscle should be used. These include the promoters from genes encoding skeletal β-actin, myosin light chain 2A, dystrophin, muscle creatine kinase, as well as synthetic muscle promoters with activities higher than naturally-occurring promoters (see Li et al., *Nat. Biotech.*, 17:241-245 (1999)). Examples of promoters that are tissue-specific are known for liver (albumin, Miyatake et al., *J. Virol.*, 71:5124-32 (1997); hepatitis B virus core promoter, Sandig et al., *Gene Ther.*, 3:1002-9 (1996); alpha-fetoprotein (AFP), Arbuthnot et al., *Hum. Gene Ther.*, 7:1503-14 (1996)), bone osteocalcin (Stein et al., *Mol. Biol. Rep.*, 24:185-96 (1997)); bone sialoprotein (Chen et al., *J. Bone Miner. Res.*, 11:654-64 (1996)), lymphocytes (CD2, Hansal et al., *J. Immunol.*, 161:1063-8 (1998); immunoglobulin heavy chain; T cell receptor α chain), neuronal such as neuron-specific enolase (NSE) promoter (Andersen et al., *Cell. Mol. Neurobiol.*, 13:503-15 (1993)), neurofilament light-chain gene (Piccioli et al., *Proc. Natl. Acad. Sci. USA*, 88:5611-5 (1991)), and the neuron-specific vgf gene (Piccioli et al., *Neuron*, 15:373-84 (1995)), among others.

Examples of suitable activatable and constitutive promoters are known to those of skill in the art. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contains the rep and/or cap proteins under the control of inducible promoters. Still other stable host cells may be generated by one of skill in the art.

Alternatively, one or more of the components required to be cultured in the host cell to package an expression cassette in an AAV capsid may be provided to the host cell in trans using a suitable genetic element.

Once a suitable cell culture system is selected, the cells are cultured in a suitable media under conditions which permit packaging of the AAV, the supernatant is collected from the culture, and the AAV isolated therefrom. In one embodiment, the invention provides a system which is scalable, allowing a cell culture to be maintained throughout a continuous production process, i.e., not requiring cell disruption and/or cell lysis for collection. In one embodiment, such a system maintains a viable cell culture. In another embodiment, the cell culture contains a mixed population of viable and non-viable cells. During the culture process, media can be added during the culturing process and/or in conjunction with collection of the supernatant to provide a continuous production process. This addition of media, fresh cells, and/or required nutritional or other elements such as a regulating agent may be repeated at least two times, from two to 100 times, or more than 100 times, depending upon the life of the cell culture.

While the method of the invention permits continuous production of the virus, upon completion of the production run, it may be desirable to extract any AAV remaining from the production cells prior to destruction thereof. This extraction can be performed using methods commonly used therefor. Such methods typically include removing the supernatant, lysing the cells by freeze/thaw or sonication techniques, following by detergent treatment (e.g., benzonase). Purification is traditionally performed by three rounds of CsCl gradient centrifugation, dialysis and concentration.

In one embodiment, the invention provides a cell culture containing cells grown in suitable culture media. Optionally, any components necessary to activate or induce expression of a desired gene product or required for virion production are supplied prior to, or at appropriate times during, production. Such components may be added with the media or supplied separately. For example, one or more suitable genetic element (e.g., a plasmid) carrying a required component(s) may be transfected into the desired cell line.

In one embodiment, the medium is a serum-free media such as Dulbecco's Modified Eagle Medium (DMEM), which contains such inorganic salts as $CaCl_2$(anhyd.), $Fe(NO_3)$ $9H_2O$, KCl, $MgSO_4$(anhyd.), NaCl, and $NaH_2PO_4$ $H_2O$, amino acids such as L-arginine HCl, L-cystine 2HCl, glutamine, glycine, histidine HCl $H_2O$, isoleucine, lysine HCl, methionine, phenylalanine, serine, threonine, tryptophan, tyrosine 2Na $2H_2O$, and valine, vitamins such as D-Ca pantothenate, choline chloride, folic acid, i-inositol, niacinamide, riboflavin, and thiamine HCl, and other components such as D-glucose, phenol red, and sodium pyruvate. Other suitable serum-free media may be selected.

A cell produced in the absence of serum (i.e., in serum-free medium) according to the invention, preferably has the additional advantage that it can be cultured in the absence of serum or serum components. Thus, isolation is easy and cost effective, safety is enhanced, and the system has good reliability (synthetic media are the best for reproducibility). The cells of the invention and, in particular, those based on primary cells, are capable of normal (for humans) post- and peri-translational modifications and assembly. This means that they are very suitable for preparing viral proteins and viruses for use in therapeutic and vaccine compositions.

In another embodiment, media containing serum may be selected. Additionally or alternatively, media may be mixed before or during the culturing process with desired nutrients, activating (inducing) agents, or serum (e.g., DMEM+10% fetal bovine serum). In still another embodiment, protein free media may be utilized.

Fresh media and any necessary inducing or activating agents are supplied (e.g., by a peristaltic pump or other suitable means) and spent media is removed from the culture vessel at the same flow rate. The culture volume is maintained and the dilution rate can be altered by changing the pump running speed. After initiation, the culture is maintained at a suitable temperature range for the selected cell culture (e.g., about room temperature to 37° C.) with stirring. The culture may be aerobic or anaerobic, depending upon the selected cell type.

It is anticipated that media will need to be added approximately 24 hours following transfection, or initiation of culturing a stable expressing cell line. However, a culture can be periodically sampled to determine the concentrations of host cells and AAV in the supernatant, to assess more precisely the timing of supernatant collection and media addition.

Thus, in one embodiment, the invention provides a continuous system for AAV viral production. In one embodiment, a batch culture is used. For example, batch culture may utilize suspension and/or adherent cells, a fed-batch culture, fill and draw. A variety of batch culture systems are known to those of skill in the art and utilize, e.g., bioreactors, fermenters, micro-carrier systems, static flasks, cell factories, roller bottles, disposable bags (e.g., the Wave™ system), stainless steel and glass vessels. Other systems, e.g., perfusion systems such as hollow fibre bioreactors, Micro-carrier systems, cell cube system (Corning), spin filters, packed bed bioreactors (e.g., Fibre cell), an cell encapsulation, can be used for AAV viral production.

In a continuous system, it is well known to those of skill in the art to obtain samples at various stages and measure the concentration of the virus by infectivity, genome titration, or other suitable methods. Once the appropriate concentration is obtained, supernatant can be drawn into the desired purification system. At the same time, appropriate amounts of replacement media and any other necessary components are supplied to the cell culture.

The AAV in the supernatant can be harvested using suitable techniques which are known to those of skill in the art. For example, monolith columns (e.g., in ion exchange, affinity or IMAC mode), chromatography (e.g., capture chromatography, fixed method chromatography, and expanded bed chromatography), filtration and precipitation, can be used for purification and concentration. These methods may be used alone or in combination. In one embodiment, capture chromatography methods, including column-based or membrane-based systems, are utilized in combination with filtration and precipitation. Suitable precipitation methods, e.g., utilizing polyethylene glycol (PEG) 8000 and $NH_3SO_4$, can be readily selected by one of skill in the art. Thereafter, the precipitate can be treated with benzonase and purified using suitable techniques.

In one embodiment, advantageously, when produced using the method of the invention, the cell culture supernatant contains significantly higher levels of AAV as compared to AAV which remains within in the cells. In certain embodiments, the supernatant comprises AAV in a yield of at least 60%.

At present, the inventors have found that AAV production efficiency has been increased by harvest of supernatant versus cell pellet for more that 30 recombinant AAV species.

Thus, the invention also provides a virus for use in a therapeutic or vaccine composition obtainable by a method or by a use according to the invention, the virus or the viral protein being free of any non-human mammalian proteinaceous material and a pharmaceutical formulation comprising such a virus and/or viral protein. Examples of such viruses include those described in the co-owned patent application, entitled "Modified AAV Vectors Having Reduced Capsid Immunogenicity And Use Thereof", filed on the same date herewith, and which claims the benefit of U.S. Provisional Patent Application No. 60/795,965, filed Apr. 28, 2006.

Thus, in one embodiment, the invention provides a kit for producing AAV as described herein. Such a kit may contain one or more of the following components. A suitable production cell capable of directing the packaging of an AAV viral particle may be supplied. Such a production cell may have been engineered to contain all of the elements required for production of the AAV. Alternatively, such a production cell may have been altered such that it lacks the ability to express heparin capable of binding to a heparin binding site. Other suitable components may include, a transfection reagent, a plasmid component for construction of a vector, a component necessary for collection, purification, concentration or harvesting of the assembled AAV particle, a reagent for negative or positive selection of viral particle in order to purify, a reagent for concentration of viral preparation, and/or a reagent for enzymatic digestion of contaminants in viral preparation.

The following examples are illustrative of methods, for producing AAV particles in the supernatant of cell cultures according to the present invention.

Example 1

Experimentals:

293 cells were transfected with $CaPO_4$ with plasmids required for production of AAV, i.e., AAV2 rep, a adenoviral helper construct and a ITR flanked transgene cassette. The AAV2 rep plasmid also contains the cap sequence of the particular virus being studied. The cap sequence is the only variable in all experiments. These experiments have been repeated for several transgene cassettes. Twenty-four hours after transfection, which occurred in serum containing DMEM, the medium was replaced with fresh medium with or without serum. Three (3) days after transfection, a sample (I) was taken from the culture medium of the 293 adherent cells. Subsequently cells were scraped and transferred into a receptacle. After centrifugation to remove cellular pellet, a sample (II) was taken from the supernatant after scraping. Next cell lysis was achieved by three consecutive freeze-thaw cycles (−80° C. to 37° C.). Cellular debris was removed and sample (III) was taken from the medium. The samples were quantified for AAV by DNase resistant genome titration by Taqman™ PCR. The total production yield from such a transfection is equal to the particle concentration from sample III. Three fractions are contained in this namely the culture supernatant fraction, the cell pellet fraction and the fraction that is released by the scraping and subsequent centrifugation of the cells. The absolute numbers of these fractions are obtained in the following way.

Particle number supernatant=particle number sample I

Particle number fraction removed by scraping and spinning (loosely cell associated)=particle number sample II minus sample I Particle number fraction in cell pellet=particle number sample III minus sample II.

Results:

The presence of the RxxR [SEQ ID NO: 12] motif (domain) not only largely restricts the localization of the AAV particles to the cellular pellet but also limits its production from the cellular substrate possibly by saturation. This limitation is not observed for non-heparin binding AAV2 homologues or AAV8 (FIGS. 1 and 2). The presence (S) or absence (SF) of serum (FIG. 2) does not seem to dramatically impact on the production of AAV particles for the non-heparin binding AAV. The saturation effect of heparin binding AAV2 on the other hand seems to be alleviated some in the presence of serum.

In another example, using prior art methods at laboratory scale, about 40 15 cm dishes would be anticipated to yield on average for AAV2/7 around $4\times10^{13}$ particles total. This current invention allows with inclusion of the supernatant to $4.7\times10^{12}$ particles to be harvested per plate.

Also, in combination with the use of serum-free medium, this technology reduces the subsequent purification effort dramatically. More particularly, AAV2/1 and AAV2/8 produced using the supernatant collection method of the invention were compared to AAV2/1 and AAV2/8 produced using previously described methods and purified via CsCl gradient. For both viruses, significantly higher infectivity was observed for the AAV2/1 and AAV2/8 particles obtained according to the supernatant collection method of the invention over a range of concentrations.

Reproducibly, for a large number of AAV isolates, DNase resistant particles from a single 15 cm dish transfection was produced with adeno-helper plasmid deltaF6, AAV rep-cap expressing trans plasmid for packaging and AAV2.CMV.eGFP cis plasmid for the vector genome. Titers for these small scale purifications for non-heparin binding isolates added up to $10^{12}$ to $10^{13}$ genome copy containing particles per plate (FIG. 3). These quantities are sufficient for most lab applications for in vitro or in vivo experimentation.

Example 2

Vector release into the supernatant was investigated for serotypes 1, 2, 3, 5, 6, 7, 8 and 9 as well as novel vectors rh32.33, rh.10, hu.11, AAV6.2, AAV6.1, AAV6.1.2, rh64R1 and rh8R. AAV2, AAV2/3 and AAV2/5 were found to secrete minimal (less than 10% of total Dnase-resistant vector genomes or particles (drp vg)). AAV2/9 is released moderately into the supernatant during viral vector production (more than 10%, less than 20% of total drp vg). All other vectors tested secrete more than 20% of their viral particles into the supernatant during production onto 293 cells following triple transfection.

The infectivity of vectors harvested from the supernatant was compared to that of purified (CsCl pure with the exception of AAV2 which was heparin purified) preparations as well as vector harvested from cellular pellet lysates. AAV harvested from the supernatant was found to be of equal or higher infectivity when compared to the two latter fractions in a 293 transduction assay for AAV vector based on isolate 1, 2, 6, 8 or 9 as well as AAV2HSPG-.

Vector release into the supernatant seems to be correlated with its heparin affinity. Ablation of this affinity by genetically mutating the native AAV2 (SEQ ID NO: 9) RGNR [SEQ ID NO: 18] heparin binding motif (into SGNT, SEQ ID NO: 19) increases the fraction of vector that is released into the supernatant by more than 40%. The introduction of the heparin binding arginines at the homologous position on the AAV8 capsid (non-heparin binding, SEQ ID NO: 11) produces the AAV8RQNR vector that is almost entirely associated with the cellular pellet during the harvest of viral vector production. This is in contrast with its parental vector AAV8 which on average releases more than 40% of its retrievable vector genome particles into the supernatant.

Example 3

An immunization study was performed to assess the effect of a variety of AAV vectors having differing capsids on T-cell activation. The study compared a native AAV6 capsid, known to have a heparin binding domain at the lysine residue at position 531 to three modified AAV having capsids with site-specific modifications introduced. These AAV, designated AAV2/6.2 (modified at a position other than K531), AAV2/6.1 (having an AAV6 capsid [SEQ ID NO: 3] modified at position 531 to contain a glutamic acid (i.e., a non-conservative amino acid change), and AAV2/6.1.2, having an AAV6 capsid with both the modifications of the AAV6.2 and AAV6.1 capsid were utilized. The sequences and generation of these vectors is described in International Patent Appln No. PCT/US06/13375. AAV1 served as a negative control and AAV2 served as a positive control.

Figure 4:
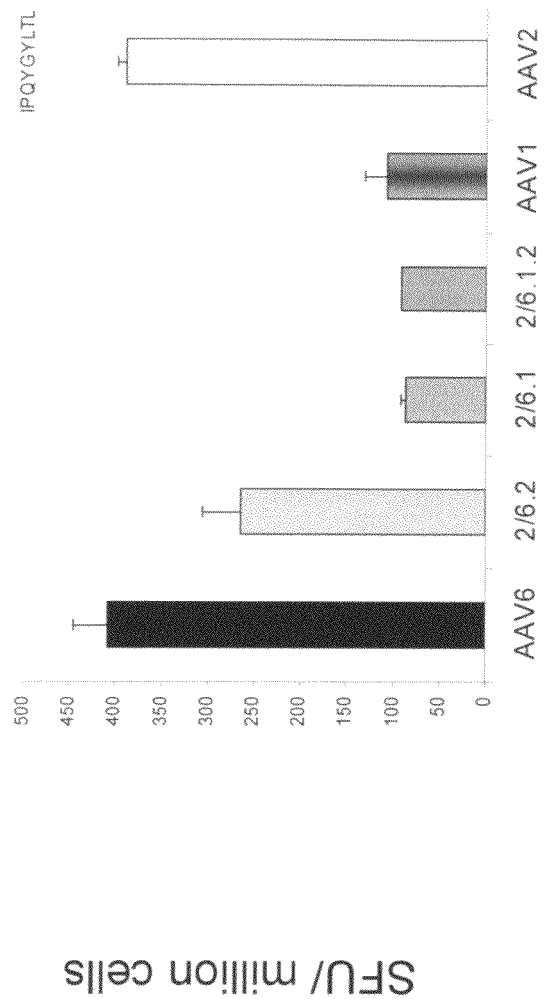
FIG. 4 is a bar chart showing the results of immunization with a variety of AAV on T-cell activation. Balb/c mice were immunized with $1\times10^{11}$ GC AAV2/6, AAV2/6.1, AAV2/6.2, AAV2/6.1.2, AAV2/1 and AAV2 vector. 13 days later splenocytes were harvested from 3 mice per group and pooled. Equal amounts of splenocytes were stimulated in vitro with the Balb/c AAV epitope IPQYGYLTL [SEQ ID NO: 1] in a ELISPOT assay.
Figure 5:
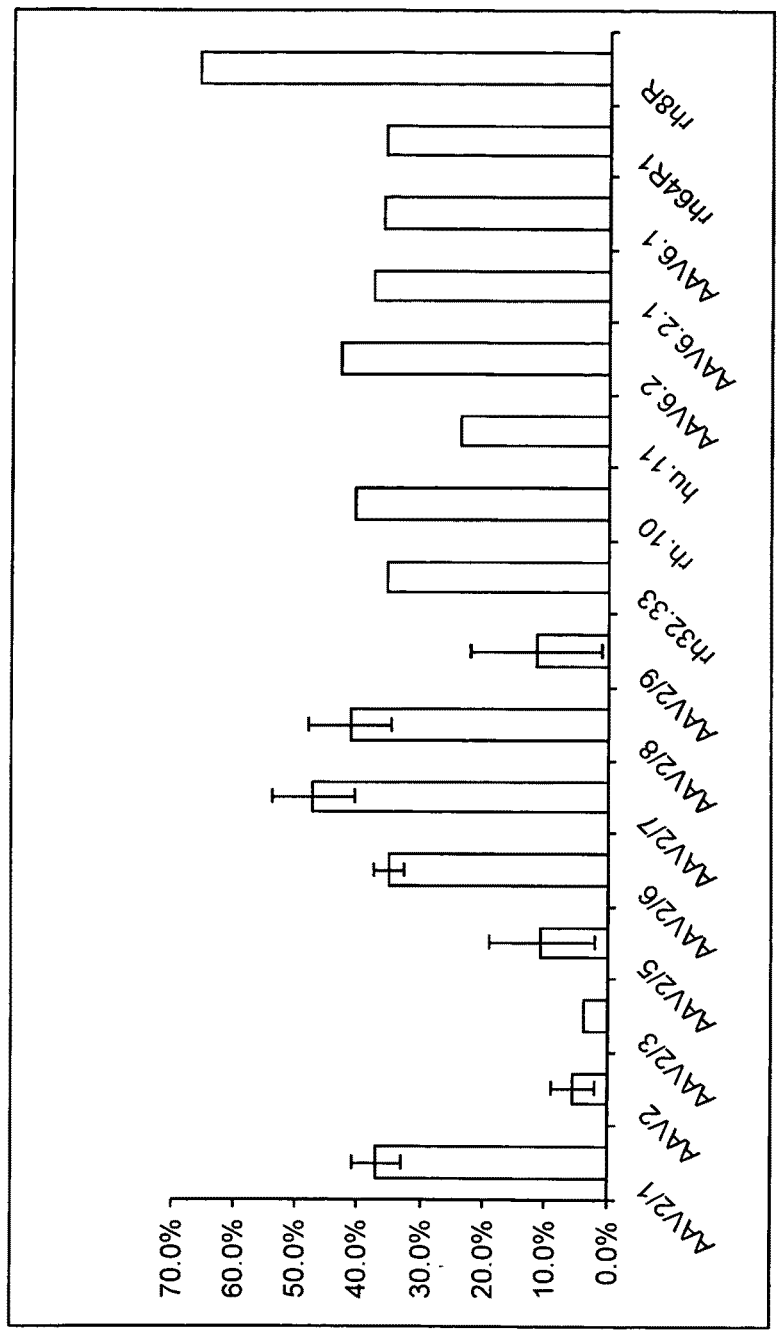
FIG. 5 is a bar chart showing the fraction of vector released into supernatant following production of the specified AAV viral vector by triple transient transfection in a 293 cell culture system.

Balb/c mice (male) were immunized intramuscularly with $1\times10^{11}$ GC AAV2/6, AAV2/6.1, AAV2/6.2, AAV2/6.1.2, AAV2/1 or AAV2 vector. Thirteen (13) days later splenocytes were harvested from 3 mice per group and pooled. Equal amounts of splenocytes were stimulated in vitro with the Balb/c AAV epitope IPQYGYLTL [SEQ ID NO: 1] in a ELISPOT assay. See, FIG. 4.

These results show that viral vector containing an unmodified AAV6 capsid induced levels of T cells comparable to those induced by the AAV2 capsid. In contrast, the modified AAV6 vectors having ablated heparin binding domains (AAV2/6.1 and AAV2/6.1.2) had T-cell responses which are virtually indistinguishable from the negative control (AAV1).

This demonstrates that changing an amino acid residue responsible for mediating heparin binding to an AAV capsid to a non-conservative amino acid residue, not only ablates heparin binding, but also, significantly reduces T cell activation.

Example 4

Several serotype AAVs were assessed for their ability to bind to an anion exchange membrane (Mustang Q, Pall Scientific) in buffers with pHs ranging from 6.0 to 9.0 and elution was monitored using a 0 to 500 mM salt gradient. High pH buffers were most suitable for the binding and elution of each of the serotypes tested (Table 1). Elution of three serotypes (AAV8, AAV7 and Rh8Rc) occurred in the 100 to 150 mM range of the gradient while two (AAV9 and Rh64R1) eluted directly following the application of the gradient. Recoveries of loaded material ranged from 50% (AAV7) to 100% (Rh64R1).

TABLE 1

Binding and Elution Characteristics of novel AAV serotypes to Mustang Q Membranes

| | Optimal pH for Binding and Elution | Elution Start Point (mM) | Optimal Elution Yield |
|---|---|---|---|
| AAV 7 | 8 | 145 | 50% |
| AAV 8 | 9 | 110 | 71% |
| AAV 9 | 8.5 | 10 | 63% |
| Rh8Rc | 9 | 110 | 67% |
| Rh64R1 | 9 | 10 | 100% |

The data show that anion exchange membrane technology is applicable for the purification of a number of AAV serotypes. Due to the high flow rates and binding capacities afforded by the membranes macroporous structure, this technology is particularly suited for purification of AAV from cell culture supernatants. The data indicate that supernatant dilution or buffer exchange will be necessary to obtain appropriate salt concentrations for AAV binding to anion-exchange membranes.

All publications cited in this specification are incorporated herein by reference. While the invention has been described with reference to particularly preferred embodiments, it will be appreciated that modifications can be made without departing from the spirit of the invention.

The invention claimed is:

1. A method for production of AAV, said method comprising:
(a) culturing mammalian cells which have been modified to prevent intracellular expression or binding of heparin in a media suitable for the cells, wherein said cells comprise:
one or more adenovirus helper functions necessary for packaging into the AAV capsid, sequences capable of expressing one or more AAV rep proteins sufficient for replication in the cell culture, sequences which express an AAV capsid in the cell culture, and a nucleic acid molecule comprising an expression cassette to be packaged into the AAV capsid, said expression cassette comprising AAV inverted terminal repeats and a heterologous nucleic acid sequence;
(b) collecting the AAV by removing spent media from the cell culture without collection of a cell pellet or cell disruption, said AAV having the nucleic acid molecule comprising the expression cassette packaged in the AAV capsid;
(c) adding media during or following collection of the spent media to maintain the cell culture and provide a continuous AAV production process; and
(d) isolating the AAV from the collected media of the cell culture.

2. The method according to claim 1, wherein the culturing step is performed in serum-free medium.

3. The method according to claim 1, wherein the AAV is cultured in a HEK 293 cell.

4. The method according to claim 1, wherein the isolating step further comprises concentrating AAV through chromatography, filtration or precipitation.

5. The method according to claim 4, wherein the chromatography is column based.

6. The method according to claim 1, wherein the cell is stably transformed with the sequences encoding the adenovirus helper functions.

7. The method according to claim 1, wherein the adenovirus helper functions are expressed under an activatable or inducible promoter.

8. The method according to claim 1, wherein the cell is stably transformed with the sequences encoding the AAV rep and/or AAV cap protein.

9. The method according to claim 8, wherein the AAV rep protein and/or the AAV cap protein are expressed under direction of an activatable or inducible promoter.

10. The method according to claim 1, wherein the cell is stably transformed with the expression cassette to be packaged.

11. The method according to claim 1, wherein the fresh spent media is added at the same rate as spent media is collected.

12. The method according to claim 1, wherein the fresh media is added starting about 24 hours following initiation of culturing the cells of claim 1 (a).

13. The method according to claim 1, wherein the isolating is performed by eluting the collected media containing the AAV over an anion exchange resin in a buffer having a pH in the range of about 6 to about 9.

14. The method according to claim 13, wherein the pH is about 8 to about 9.

15. The method according to claim 13, wherein the elution is performed using a 0 to 500 mM salt gradient.

16. The method according to claim 15, wherein the elution is performed using a 100 to 150 mM salt gradient.

* * * * *

SEQUENCE LISTING

```
<160> NUMBER OF SEQ ID NOS: 19

<210> SEQ ID NO 1
<211> LENGTH: 9
<212> TYPE: PRT
<213> ORGANISM: Unknown
<220> FEATURE:
<223> OTHER INFORMATION: Balb/c AAV epitope

<400> SEQUENCE: 1

Ile Pro Gln Tyr Gly Tyr Leu Thr Leu
1               5

<210> SEQ ID NO 2
<211> LENGTH: 736
<212> TYPE: PRT
<213> ORGANISM: Human adenovirus type 1

<400> SEQUENCE: 2

Met Ala Ala Asp Gly Tyr Leu Pro Asp Trp Leu Glu Asp Asn Leu Ser
1               5                  10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205
```

```
Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
            325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
            405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
            485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Glu Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
            565                 570                 575

Phe Gly Thr Val Ala Val Asn Phe Gln Ser Ser Ser Thr Asp Pro Ala
            580                 585                 590

Thr Gly Asp Val His Ala Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620
```

-continued

```
Thr Asp Gly His Phe His Pro Ser Pro Leu Met Gly Gly Phe Gly Leu
625                 630                 635                 640

Lys Asn Pro Pro Gln Ile Leu Ile Lys Asn Thr Pro Val Pro Ala
            645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
            690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 3
<211> LENGTH: 736
<212> TYPE: PRT
<213> ORGANISM: Human adenovirus type 6

<400> SEQUENCE: 3

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270
```

```
Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
        290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
                355                 360                 365

Asp Val Phe Met Ile Pro Gln Tyr Gly Tyr Leu Thr Leu Asn Asn Gly
        370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
                435                 440                 445

Thr Gln Asn Gln Ser Gly Ser Ala Gln Asn Lys Asp Leu Leu Phe Ser
            450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
            515                 520                 525

Asp Asp Lys Asp Lys Phe Phe Pro Met Ser Gly Val Met Ile Phe Gly
            530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
            595                 600                 605

Asp Arg Asp Val Tyr Leu Gln Gly Pro Ile Trp Ala Lys Ile Pro His
        610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
            675                 680                 685
```

```
Lys Glu Asn Ser Lys Arg Trp Asn Pro Glu Val Gln Tyr Thr Ser Asn
    690                 695                 700
Tyr Ala Lys Ser Ala Asn Val Asp Phe Thr Val Asp Asn Asn Gly Leu
705                 710                 715                 720
Tyr Thr Glu Pro Arg Pro Ile Gly Thr Arg Tyr Leu Thr Arg Pro Leu
                725                 730                 735

<210> SEQ ID NO 4
<211> LENGTH: 733
<212> TYPE: PRT
<213> ORGANISM: Unknown
<220> FEATURE:
<223> OTHER INFORMATION: vp1, clone rh.32.33

<400> SEQUENCE: 4

Met Ala Ala Asp Gly Tyr Leu Pro Asp Trp Leu Glu Asp Asn Leu Ser
1                   5                   10                  15
Glu Gly Ile Arg Glu Trp Trp Asp Leu Lys Pro Gly Ala Pro Lys Leu
                20                  25                  30
Lys Ala Asn Gln Gln Lys Gln Asp Asp Gly Arg Gly Leu Val Leu Pro
            35                  40                  45
Gly Tyr Lys Tyr Leu Gly Pro Phe His Gly Leu Asp Lys Gly Glu Pro
50                  55                  60
Val Asn Ala Ala Asp Ala Ala Ala Leu Glu His Asp Lys Ala Tyr Asp
65                  70                  75                  80
Gln Gln Leu Lys Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Gly Ala Lys Thr Ala Pro Gly Lys Lys Arg
130                 135                 140
Pro Leu Glu Ser Pro Gln Glu Pro Asp Ser Ser Ser Gly Ile Gly Lys
145                 150                 155                 160
Lys Gly Lys Gln Pro Ala Lys Lys Arg Leu Asn Phe Glu Glu Asp Thr
                165                 170                 175
Gly Ala Gly Asp Gly Pro Pro Glu Gly Ser Asp Thr Ser Ala Met Ser
            180                 185                 190
Ser Asp Ile Glu Met Arg Ala Ala Pro Gly Gly Asn Ala Val Asp Ala
        195                 200                 205
Gly Gln Gly Ser Asp Gly Val Gly Asn Ala Ser Gly Asp Trp His Cys
210                 215                 220
Asp Ser Thr Trp Ser Glu Gly Lys Val Thr Thr Thr Ser Thr Arg Thr
225                 230                 235                 240
Trp Val Leu Pro Thr Tyr Asn Asn His Leu Tyr Leu Arg Leu Gly Thr
                245                 250                 255
Thr Ser Asn Ser Asn Thr Tyr Asn Gly Phe Ser Thr Pro Trp Gly Tyr
            260                 265                 270
Phe Asp Phe Asn Arg Phe His Cys His Phe Ser Pro Arg Asp Trp Gln
        275                 280                 285
Arg Leu Ile Asn Asn Asn Trp Gly Leu Arg Pro Lys Ala Met Arg Val
290                 295                 300
Lys Ile Phe Asn Ile Gln Val Lys Glu Val Thr Thr Ser Asn Gly Glu
305                 310                 315                 320
```

```
Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
        355                 360                 365

Cys Gly Ile Val Thr Gly Glu Asn Gln Asn Gln Thr Asp Arg Asn Ala
370                 375                 380

Phe Tyr Cys Leu Glu Tyr Phe Pro Ser Gln Met Leu Arg Thr Gly Asn
385                 390                 395                 400

Asn Phe Glu Met Ala Tyr Asn Phe Glu Lys Val Pro Phe His Ser Met
                405                 410                 415

Tyr Ala His Ser Gln Ser Leu Asp Arg Leu Met Asn Pro Leu Leu Asp
            420                 425                 430

Gln Tyr Leu Trp His Leu Gln Ser Thr Thr Ser Gly Glu Thr Leu Asn
        435                 440                 445

Gln Gly Asn Ala Ala Thr Thr Phe Gly Lys Ile Arg Ser Gly Asp Phe
450                 455                 460

Ala Phe Tyr Arg Lys Asn Trp Leu Pro Gly Pro Cys Val Lys Gln Gln
465                 470                 475                 480

Arg Phe Ser Lys Thr Ala Ser Gln Asn Tyr Lys Ile Pro Ala Ser Gly
                485                 490                 495

Gly Asn Ala Leu Leu Lys Tyr Asp Thr His Tyr Thr Leu Asn Asn Arg
            500                 505                 510

Trp Ser Asn Ile Ala Pro Gly Pro Pro Met Ala Thr Ala Gly Pro Ser
        515                 520                 525

Asp Gly Asp Phe Ser Asn Ala Gln Leu Ile Phe Pro Gly Pro Ser Val
530                 535                 540

Thr Gly Asn Thr Thr Thr Ser Ala Asn Asn Leu Leu Phe Thr Ser Glu
545                 550                 555                 560

Gly Glu Ile Ala Ala Thr Asn Pro Arg Asp Thr Asp Met Phe Gly Gln
                565                 570                 575

Ile Ala Asp Asn Asn Gln Asn Ala Thr Thr Ala Pro Ile Thr Gly Asn
            580                 585                 590

Val Thr Ala Met Gly Val Leu Pro Gly Met Val Trp Gln Asn Arg Asp
        595                 600                 605

Ile Tyr Tyr Gln Gly Pro Ile Trp Ala Lys Ile Pro His Ala Asp Gly
610                 615                 620

His Phe His Pro Ser Pro Leu Ile Gly Gly Phe Gly Leu Lys His Pro
625                 630                 635                 640

Pro Pro Gln Ile Phe Ile Lys Asn Thr Pro Val Pro Ala Asn Pro Ala
                645                 650                 655

Thr Thr Phe Thr Ala Ala Arg Val Asp Ser Phe Ile Thr Gln Tyr Ser
            660                 665                 670

Thr Gly Gln Val Ala Val Gln Ile Glu Trp Glu Ile Glu Lys Glu Arg
        675                 680                 685

Ser Lys Arg Arg Asn Pro Glu Val Gln Phe Thr Ser Asn Tyr Gly Asn
690                 695                 700

Gln Ser Ser Met Leu Trp Ala Pro Asp Thr Thr Gly Lys Tyr Thr Glu
705                 710                 715                 720

Pro Arg Val Ile Gly Ser Arg Tyr Leu Thr Asn His Leu
                725                 730
```

```
<210> SEQ ID NO 5
<211> LENGTH: 738
<212> TYPE: PRT
<213> ORGANISM: Unknown
<220> FEATURE:
<223> OTHER INFORMATION: vp1, clone rh.10

<400> SEQUENCE: 5

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln G

```
                370                 375                 380
Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Gln Asn Ala Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 6
<211> LENGTH: 738
<212> TYPE: PRT
<213> ORGANISM: Unknown
<220> FEATURE:
<223> OTHER INFORMATION: vp1, clone rh.64

<400> SEQUENCE: 6
```

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
                35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
        130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Ala Pro Ser Ser Val Gly Ser Gly Thr Met Ala Ala Gly Gly
            195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
                260                 265                 270

Asn Thr Tyr Phe Gly Tyr Ser Thr Pro Trp Gly Tyr Phe Asp Phe Asn
            275                 280                 285

Arg Phe His Cys His Phe Ser Pro Arg Asp Trp Gln Arg Leu Ile Asn
        290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Ser Phe Ser Tyr
                405                 410                 415
```

Thr Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
    450                 455                 460

Phe Ser Gln Ala Gly Pro Ser Asn Met Ser Ala Gln Ala Arg Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

Asn Lys Asp Asp Glu Asp Arg Phe Phe Pro Ser Ser Gly Ile Leu Met
    530                 535                 540

Phe Gly Lys Gln Gly Ala Gly Lys Asp Asn Val Asp Tyr Ser Asn Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Gln Asn Thr Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Ala Phe Asn Gln Ala Lys Leu Asn Ser Phe
            660                 665                 670

Ile Thr Gln Tyr Ser Thr Gly Gln Val Ser Val Glu Ile Val Trp Glu
        675                 680                 685

Leu Gln Lys Glu Asn Ser Lys Arg Arg Asn Pro Glu Ile Gln Tyr Thr
    690                 695                 700

Ser Asn Tyr Tyr Lys Ser Thr Asn Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 7
<211> LENGTH: 736
<212> TYPE: PRT
<213> ORGANISM: Unknown
<220> FEATURE:
<223> OTHER INFORMATION: vp1, clone rh.8

<400> SEQUENCE: 7

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro

```
                35                  40                  45
Gly Tyr Lys Tyr Leu Gly Pro Phe Asn Gly Leu Asp Lys Gly Glu Pro
 50                  55                  60

Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Arg Tyr Asn His Ala
                 85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
                115                 120                 125

Leu Gly Leu Val Glu Glu Gly Ala Lys Thr Ala Pro Gly Lys Lys Arg
130                 135                 140

Pro Val Glu Gln Ser Pro Gln Glu Pro Asp Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
                180                 185                 190

Ala Ala Pro Ser Gly Leu Gly Pro Asn Thr Met Ala Ser Gly Gly Gly
                195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Gly Thr Ser Gly Gly Ser Thr Asn Asp Asn
                260                 265                 270

Thr Tyr Phe Gly Tyr Ser Thr Pro Trp Gly Tyr Phe Asp Phe Asn Arg
                275                 280                 285

Phe His Cys His Phe Ser Pro Arg Asp Trp Gln Arg Leu Ile Asn Asn
                290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Glu Gly Thr Lys Thr Ile Ala Asn
                325                 330                 335

Asn Leu Thr Ser Thr Val Gln Val Phe Thr Asp Ser Glu Tyr Gln Leu
                340                 345                 350

Pro Tyr Val Leu Gly Ser Ala His Gln Gly Cys Leu Pro Pro Phe Pro
                355                 360                 365

Ala Asp Val Phe Met Val Pro Gln Tyr Gly Tyr Leu Thr Leu Asn Asn
                370                 375                 380

Gly Ser Gln Ala Leu Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Thr
                405                 410                 415

Phe Glu Asp Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Val
                435                 440                 445

Arg Thr Gln Thr Thr Gly Thr Gly Gly Thr Gln Thr Leu Ala Phe Ser
                450                 455                 460
```

Gln Ala Gly Pro Ser Ser Met Ala Asn Gln Ala Arg Asn Trp Val Pro
465                 470                 475                 480

Gly Pro Cys Tyr Arg Gln Gln Arg Val Ser Thr Thr Asn Gln Asn
        485                 490                 495

Asn Asn Ser Asn Phe Ala Trp Thr Gly Ala Ala Lys Phe Lys Leu Asn
            500                 505                 510

Gly Arg Asp Ser Leu Met Asn Pro Gly Val Ala Met Ala Ser His Lys
        515                 520                 525

Asp Asp Asp Asp Arg Phe Phe Pro Ser Ser Gly Val Leu Ile Phe Gly
530                 535                 540

Lys Gln Gly Ala Gly Asn Asp Gly Val Asp Tyr Ser Gln Val Leu Ile
545                 550                 555                 560

Thr Asp Glu Glu Glu Ile Lys Ala Thr Asn Pro Val Ala Thr Glu Glu
                565                 570                 575

Tyr Gly Ala Val Ala Ile Asn Asn Gln Ala Ala Asn Thr Gln Ala Gln
                580                 585                 590

Thr Gly Leu Val His Asn Gln Gly Val Ile Pro Gly Met Val Trp Gln
        595                 600                 605

Asn Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asp Pro Pro Leu Thr Phe Asn Gln Ala Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
690                 695                 700

Tyr Tyr Lys Ser Thr Asn Val Asp Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 8
<211> LENGTH: 736
<212> TYPE: PRT
<213> ORGANISM: Human adenovirus type 9

<400> SEQUENCE: 8

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly

-continued

```
                100                 105                 110
Asn Leu Gly Arg Ala Val Phe Gln Ala Lys Lys Arg Leu Leu Glu Pro
            115                 120                 125
Leu Gly Leu Val Glu Glu Ala Ala Lys Thr Ala Pro Gly Lys Lys Arg
        130                 135                 140
Pro Val Glu Gln Ser Pro Gln Glu Pro Asp Ser Ser Ala Gly Ile Gly
145                 150                 155                 160
Lys Ser Gly Ala Gln Pro Ala Lys Lys Arg Leu Asn Phe Gly Gln Thr
                165                 170                 175
Gly Asp Thr Glu Ser Val Pro Asp Pro Gln Pro Ile Gly Glu Pro Pro
            180                 185                 190
Ala Ala Pro Ser Gly Val Gly Ser Leu Thr Met Ala Ser Gly Gly Gly
        195                 200                 205
Ala Pro Val Ala Asp Asn Asn Glu Gly Ala Asp Gly Val Gly Ser Ser
    210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Ser Thr Ser Gly Gly Ser Ser Asn Asp Asn
            260                 265                 270
Ala Tyr Phe Gly Tyr Ser Thr Pro Trp Gly Tyr Phe Asp Phe Asn Arg
        275                 280                 285
Phe His Cys His Phe Ser Pro Arg Asp Trp Gln Arg Leu Ile Asn Asn
    290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                325                 330                 335
Asn Leu Thr Ser Thr Val Gln Val Phe Thr Asp Ser Asp Tyr Gln Leu
            340                 345                 350
Pro Tyr Val Leu Gly Ser Ala His Glu Gly Cys Leu Pro Pro Phe Pro
        355                 360                 365
Ala Asp Val Phe Met Ile Pro Gln Tyr Gly Tyr Leu Thr Leu Asn Asp
    370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Ser
        435                 440                 445
Lys Thr Ile Asn Gly Ser Gly Gln Asn Gln Gln Thr Leu Lys Phe Ser
    450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                485                 490                 495
Asn Asn Ser Glu Phe Ala Trp Pro Gly Ala Ser Ser Trp Ala Leu Asn
            500                 505                 510
Gly Arg Asn Ser Leu Met Asn Pro Gly Pro Ala Met Ala Ser His Lys
        515                 520                 525
```

```
Glu Gly Glu Asp Arg Phe Phe Pro Leu Ser Gly Ser Leu Ile Phe Gly
        530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 9
<211> LENGTH: 735
<212> TYPE: PRT
<213> ORGANISM: Human adenovirus type 2

<400> SEQUENCE: 9

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
```

```
                  165                 170                 175
Gly Asp Ala Asp Ser Val Pro Asp Pro Gln Pro Leu Gly Gln Pro Pro
                180                 185                 190

Ala Ala Pro Ser Gly Leu Gly Thr Asn Thr Met Ala Thr Gly Ser Gly
                195                 200                 205

Ala Pro Met Ala Asp Asn Asn Glu Gly Ala Asp Gly Val Gly Asn Ser
            210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
                275                 280                 285

Cys His Phe Ser Pro Arg Asp Trp Gln Arg Leu Ile Asn Asn Asn Trp
            290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
                355                 360                 365

Val Phe Met Val Pro Gln Tyr Gly Tyr Leu Thr Leu Asn Asn Gly Ser
            370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
                450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
                515                 520                 525

Asp Glu Glu Lys Phe Phe Pro Gln Ser Gly Val Leu Ile Phe Gly Lys
                530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590
```

```
Ala Asp Val Asn Thr Gln Gly Val Leu Pro Gly Met Val Trp Gln Asp
            595                 600                 605

Arg Asp Val Tyr Leu Gln Gly Pro Ile Trp Ala Lys Ile Pro His Thr
            610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
            645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
            675                 680                 685

Glu Asn Ser Lys Arg Trp Asn Pro Glu Ile Gln Tyr Thr Ser Asn Tyr
            690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
            725                 730                 735

<210> SEQ ID NO 10
<211> LENGTH: 736
<212> TYPE: PRT
<213> ORGANISM: Human adenovirus type 3

<400> SEQUENCE: 10

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
            35                  40                  45

Gly Tyr Lys Tyr Leu Gly Pro Gly Asn Gly Leu Asp Lys Gly Glu Pro
50                  55                  60

Val Asn Glu Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
            85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
            115                 120                 125

Leu Gly Leu Val Glu Glu Ala Ala Lys Thr Ala Pro Gly Lys Lys Gly
            130                 135                 140

Ala Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
            165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
            195                 200                 205

Ala Pro Met Ala Asp Asn Asn Glu Gly Ala Asp Gly Val Gly Asn Ser
210                 215                 220

Ser Gly Asn Trp His Cys Asp Ser Gln Trp Leu Gly Asp Arg Val Ile
```

```
            225                 230                 235                 240

Thr Thr Ser Thr Arg Thr Trp Ala Leu Pro Thr Tyr Asn Asn His Leu
                        245                 250                 255

Tyr Lys Gln Ile Ser Ser Gln Ser Gly Ala Ser Asn Asp Asn His Tyr
                        260                 265                 270

Phe Gly Tyr Ser Thr Pro Trp Gly Tyr Phe Asp Phe Asn Arg Phe His
                        275                 280                 285

Cys His Phe Ser Pro Arg Asp Trp Gln Arg Leu Ile Asn Asn Asn Trp
                        290                 295                 300

Gly Phe Arg Pro Lys Lys Leu Ser Phe Lys Leu Phe Asn Ile Gln Val
        305                 310                 315                 320

Arg Gly Val Thr Gln Asn Asp Gly Thr Thr Thr Ile Ala Asn Asn Leu
                        325                 330                 335

Thr Ser Thr Val Gln Val Phe Thr Asp Ser Glu Tyr Gln Leu Pro Tyr
                        340                 345                 350

Val Leu Gly Ser Ala His Gln Gly Cys Leu Pro Pro Phe Pro Ala Asp
                        355                 360                 365

Val Phe Met Val Pro Gln Tyr Gly Tyr Leu Thr Leu Asn Asn Gly Ser
                        370                 375                 380

Gln Ala Val Gly Arg Ser Ser Phe Tyr Cys Leu Glu Tyr Phe Pro Ser
        385                 390                 395                 400

Gln Met Leu Arg Thr Gly Asn Asn Phe Gln Phe Ser Tyr Thr Phe Glu
                        405                 410                 415

Asp Val Pro Phe His Ser Ser Tyr Ala His Ser Gln Ser Leu Asp Arg
                        420                 425                 430

Leu Met Asn Pro Leu Ile Asp Gln Tyr Leu Tyr Tyr Leu Asn Arg Thr
                        435                 440                 445

Gln Gly Thr Thr Ser Gly Thr Thr Asn Gln Ser Arg Leu Leu Phe Ser
                        450                 455                 460

Gln Ala Gly Pro Gln Ser Met Ser Leu Gln Ala Arg Asn Trp Leu Pro
        465                 470                 475                 480

Gly Pro Cys Tyr Arg Gln Gln Arg Leu Ser Lys Thr Ala Asn Asp Asn
                        485                 490                 495

Asn Asn Ser Asn Phe Pro Trp Thr Ala Ala Ser Lys Tyr His Leu Asn
                        500                 505                 510

Gly Arg Asp Ser Leu Val Asn Pro Gly Pro Ala Met Ala Ser His Lys
                        515                 520                 525

Asp Asp Glu Glu Lys Phe Phe Pro Met His Gly Asn Leu Ile Phe Gly
                        530                 535                 540

Lys Glu Gly Thr Thr Ala Ser Asn Ala Glu Leu Asp Asn Val Met Ile
        545                 550                 555                 560

Thr Asp Glu Glu Glu Ile Arg Thr Thr Asn Pro Val Ala Thr Glu Gln
                        565                 570                 575

Tyr Gly Thr Val Ala Asn Asn Leu Gln Ser Ser Asn Thr Ala Pro Thr
                        580                 585                 590

Thr Gly Thr Val Asn His Gln Gly Ala Leu Pro Gly Met Val Trp Gln
                        595                 600                 605

Asp Arg Asp Val Tyr Leu Gln Gly Pro Ile Trp Ala Lys Ile Pro His
                        610                 615                 620

Thr Asp Gly His Phe His Pro Ser Pro Leu Met Gly Gly Phe Gly Leu
        625                 630                 635                 640

Lys His Pro Pro Pro Gln Ile Met Ile Lys Asn Thr Pro Val Pro Ala
                        645                 650                 655
```

```
Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
            690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
                725                 730                 735

<210> SEQ ID NO 11
<211> LENGTH: 738
<212> TYPE: PRT
<213> ORGANISM: Human adenovirus type 8

<400> SEQUENCE: 11

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
            85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
            165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
            245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
```

```
                290                 295                 300
Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
                340                 345                 350

Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
        370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
            435                 440                 445

Ser Arg Thr Gln Thr Thr Gly Gly Thr Ala Asn Thr Gln Thr Leu Gly
        450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
                500                 505                 510

Leu Asn Gly Arg Asn Ser Leu Ala Asn Pro Gly Ile Ala Met Ala Thr
            515                 520                 525

His Lys Asp Asp Glu Glu Arg Phe Phe Pro Ser Asn Gly Ile Leu Ile
        530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Asn Thr Ala
                580                 585                 590

Pro Gln Ile Gly Thr Val Asn Ser Gln Gly Ala Leu Pro Gly Met Val
            595                 600                 605

Trp Gln Asn Arg Asp Val Tyr Leu Gln Gly Pro Ile Trp Ala Lys Ile
        610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
                660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
        690                 695                 700

Ser Asn Tyr Tyr Lys Ser Thr Ser Val Asp Phe Ala Val Asn Thr Glu
705                 710                 715                 720
```

```
Gly Val Tyr Ser Glu Pro Arg Pro Ile Gly Thr Arg Tyr Leu Thr Arg
                725                 730                 735

Asn Leu

<210> SEQ ID NO 12
<211> LENGTH: 4
<212> TYPE: PRT
<213> ORGANISM: Unknown
<220> FEATURE:
<223> OTHER INFORMATION: chemically synthesized heparin binding domain
<220> FEATURE:
<221> NAME/KEY: MISC_FEATURE
<222> LOCATION: (2)..(2)
<223> OTHER INFORMATION: can be any amino acid
<220> FEATURE:
<221> NAME/KEY: MISC_FEATURE
<222> LOCATION: (3)..(3)
<223> OTHER INFORMATION: can be any amino acid

<400> SEQUENCE: 12

Arg Xaa Xaa Arg
1

<210> SEQ ID NO 13
<211> LENGTH: 735
<212> TYPE: PRT
<213> ORGANISM: Unknown
<220> FEATURE:
<223> OTHER INFORMATION: vp1, clone hu.51

<400> SEQUENCE: 13

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Gly Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220
```

```
Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
            290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Ile Ala Asn Asn Leu
            325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
            405                 410                 415

Asp Val Pro Phe His Ser Gly Tyr Ala His Ser Gln Ser Leu Asp Arg
            420                 425                 430

Leu Met Asn Pro Leu Ile Asp Gln Tyr Leu Tyr Tyr Leu Ser Thr Thr
            435                 440                 445

Asn Thr Pro Ser Gly Thr Thr Thr Gln Ser Arg Leu Gln Phe Ser Gln
            450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
            485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
            515                 520                 525

Asn Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
            565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
            595                 600                 605

Arg Asp Val Tyr Leu Gln Gly Pro Ile Trp Ala Lys Ile Pro His Thr
            610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
```

```
                          645                 650                 655
Pro Ser Thr Thr Phe Ser Ala Ala Lys Phe Ala Ser Phe Ile Thr Gln
                660                 665                 670

Tyr Ser Thr Gly Gln Val Ser Val Glu Ile Glu Trp Glu Leu Gln Lys
            675                 680                 685

Glu Asn Ser Lys Arg Trp Asn Pro Glu Ile Gln Tyr Thr Ser Asn Tyr
        690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 14
<211> LENGTH: 735
<212> TYPE: PRT
<213> ORGANISM: Unknown
<220> FEATURE:
<223> OTHER INFORMATION: vp1, clone hu.34

<400> SEQUENCE: 14

Met Ala Ala Asp Gly Tyr Leu Pro Asp Trp Leu Glu Asp Thr Leu Ser
1               5                   10                  15

Glu Gly Ile Arg Gln Arg Trp Lys Leu Lys Pro Gly Pro Pro Pro Pro
            20                  25                  30

Glu Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
```

-continued

```
              275                 280                 285
Cys His Phe Ser Pro Arg Asp Trp Gln Arg Leu Ile Asn Asn Asn Trp
290                 295                 300
Gly Phe Arg Pro Lys Arg Leu Asn Phe Lys Leu Phe Asn Ile Gln Val
305                 310                 315                 320
Lys Glu Val Thr Gln Asn Asp Gly Thr Thr Thr Ile Ala Asn Asn Leu
                    325                 330                 335
Thr Ser Thr Val Gln Val Phe Thr Asp Ser Glu Tyr Gln Leu Pro Tyr
                340                 345                 350
Val Leu Gly Ser Ala His Gln Gly Cys Leu Pro Pro Phe Pro Ala Asp
                355                 360                 365
Val Phe Met Val Pro Gln Tyr Gly Tyr Leu Thr Leu Asn Asn Glu Ser
370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                    405                 410                 415
Asp Val Pro Phe His Ser Ser Tyr Ala His Ser Gln Ser Leu Gly Arg
                420                 425                 430
Leu Met Asn Pro Leu Ile Asp Gln Tyr Leu Tyr Tyr Leu Ser Arg Thr
                435                 440                 445
Asn Thr Pro Ser Gly Thr Thr Thr Gln Ser Arg Leu Gln Phe Ser Gln
450                 455                 460
Ala Gly Ala Ser Asp Ile Arg Asp Gln Ser Arg Asn Trp Leu Pro Gly
465                 470                 475                 480
Pro Cys Tyr Arg Gln Gln Arg Val Ser Lys Thr Ser Ala Asp Asn Asn
                    485                 490                 495
Asn Ser Glu Tyr Ser Trp Thr Gly Ala Thr Lys Tyr His Leu Asn Gly
                500                 505                 510
Arg Asp Ser Leu Val Asn Pro Gly Pro Ala Met Ala Ser His Lys Asp
                515                 520                 525
Asp Glu Glu Lys Phe Phe Pro Gln Ser Gly Val Leu Ile Phe Gly Lys
530                 535                 540
Gln Gly Ser Glu Lys Thr Asn Val Asp Ile Glu Lys Val Met Ile Thr
545                 550                 555                 560
Asp Glu Glu Glu Ile Arg Thr Thr Asn Pro Val Ala Thr Glu Gln Tyr
                    565                 570                 575
Gly Ser Val Ser Thr Asn Leu Gln Arg Gly Asn Arg Gln Ala Ala Thr
                580                 585                 590
Ala Asp Val Asn Thr Gln Gly Val Leu Pro Gly Met Val Trp Gln Asp
                595                 600                 605
Arg Asp Val Tyr Leu Gln Gly Pro Ile Trp Ala Lys Ile Pro His Thr
                610                 615                 620
Asp Gly His Phe His Pro Ser Pro Leu Met Gly Gly Phe Gly Leu Lys
625                 630                 635                 640
His Pro Pro Pro Gln Ile Leu Ile Lys Asn Thr Pro Val Pro Ala Asn
                    645                 650                 655
Pro Ser Thr Thr Phe Ser Ala Ala Lys Phe Ala Ser Phe Ile Thr Gln
                660                 665                 670
Tyr Ser Thr Gly Gln Val Ser Val Glu Ile Glu Trp Glu Leu Gln Lys
                675                 680                 685
Glu Asn Ser Lys Arg Trp Asn Pro Glu Ile Gln Tyr Thr Ser Asn Tyr
690                 695                 700
```

-continued

```
Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
            725                 730                 735

<210> SEQ ID NO 15
<211> LENGTH: 735
<212> TYPE: PRT
<213> ORGANISM: Unknown
<220> FEATURE:
<223> OTHER INFORMATION: vp1, clone hu.35

<400> SEQUENCE: 15

Met Ala Ala Asp Gly Tyr Leu Pro Asp Trp Leu Glu Asp Thr Leu Ser
1               5                   10                  15

Glu Gly Ile Arg Gln Arg Trp Lys Leu Lys Pro Gly Pro Pro Pro
            20                  25                  30

Glu Pro Ala Glu Arg His Lys Asp Asp Ser Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335
```

-continued

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Phe Pro Ala Asp
                355                 360             365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Gly Arg
                420                 425                 430

Leu Met Asn Pro Leu Ile Asp Gln Tyr Leu Tyr Tyr Leu Ser Arg Thr
                435                 440                 445

Asn Thr Pro Ser Gly Thr Thr Thr Gln Ser Arg Leu Gln Phe Ser Gln
                450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
                500                 505                 510

Arg Asp Ser Leu Val Asn Pro Gly Pro Ala Met Ala Ser His Lys Asp
                515                 520                 525

Asp Glu Glu Lys Phe Phe Pro Gln Ser Gly Val Leu Ile Phe Gly Lys
                530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
                580                 585                 590

Ala Asp Val Asn Thr Gln Gly Val Leu Pro Gly Met Val Trp Gln Asp
                595                 600                 605

Arg Asp Val Tyr Leu Gln Gly Pro Ile Trp Ala Lys Ile Pro His Thr
                610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
                660                 665                 670

Tyr Ser Thr Gly Gln Val Ser Val Glu Ile Glu Trp Glu Leu Gln Lys
                675                 680                 685

Glu Asn Ser Lys Arg Trp Asn Pro Glu Ile Gln Tyr Thr Ser Asn Tyr
                690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 16
<211> LENGTH: 735

```
<212> TYPE: PRT
<213> ORGANISM: Unknown
<220> FEATURE:
<223> OTHER INFORMATION: vp1, clone hu.45

<400> SEQUENCE: 16
```

| | | | | | | | | | | | | | | |
|---|---|---|---|---|---|---|---|---|---|---|---|---|---|---|
| Met | Ala | Ala | Asp | Gly | Tyr | Leu | Pro | Asp | Trp | Leu | Glu | Asp | Thr | Leu | Ser |
| 1 | | | | 5 | | | | | 10 | | | | | 15 | |

Glu Gly Ile Arg Gln Trp Trp L

```
Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
            405                 410                 415

Asp Val Pro Phe His Ser Ser Tyr Ala His Ser Gln Ser Leu Asp Arg
        420                 425                 430

Leu Met Asn Pro Leu Ile Asp Gln Tyr Leu Tyr Tyr Leu Ser Thr Thr
    435                 440                 445

Asn Thr Pro Ser Gly Thr Thr Thr Gln Ser Arg Leu Gln Phe Ser Gln
450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
            485                 490                 495

Asn Ser Glu Tyr Ser Trp Thr Gly Ala Thr Lys Tyr His Leu Asn Gly
        500                 505                 510

Arg Asp Ser Leu Val Asn Pro Gly Pro Ala Val Ala Ser His Lys Asp
    515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
            565                 570                 575

Gly Ser Val Ser Thr Asn Leu Gln Arg Gly Asn Arg Gln Ala Ala Thr
        580                 585                 590

Ala Asp Val Asn Thr Gln Gly Val Leu Pro Gly Met Val Trp Gln Asp
    595                 600                 605

Arg Asp Val Tyr Leu Gln Gly Pro Ile Trp Ala Lys Ile Pro His Thr
610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
            645                 650                 655

Pro Ser Thr Thr Phe Ser Ala Ala Lys Phe Ala Ser Phe Ile Thr Gln
        660                 665                 670

Tyr Ser Thr Gly Gln Val Ser Val Glu Ile Glu Trp Glu Leu Gln Lys
    675                 680                 685

Glu Asn Ser Lys Arg Trp Asn Pro Glu Ile Gln Tyr Thr Ser Asn Tyr
690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
            725                 730                 735

<210> SEQ ID NO 17
<211> LENGTH: 735
<212> TYPE: PRT
<213> ORGANISM: Unknown
<220> FEATURE:
<223> OTHER INFORMATION: vp1, clone hu.47

<400> SEQUENCE: 17

Met Ala Ala Asp Gly Tyr Leu Pro Asp Trp Leu Glu Asp Thr Leu Ser
1               5                   10                  15
```

-continued

Glu Gly Ile Arg Gln Trp Trp Lys Leu Lys Pro Gly Pro Pro Pro
            20                  25                  30

Lys Pro Ala Glu Arg His Arg Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Gly Glu Pro Val Lys Thr Ala Pro Gly Lys Lys Arg
    130                 135                 140

Pro Val Glu His Ser Pro Val Glu Pro Asp Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Ser His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Thr Thr

```
                    435                 440                 445
Asn Thr Pro Ser Gly Thr Thr Thr Gln Ser Arg Leu Gln Phe Ser Gln
450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                    485                 490                 495

Asn Ser Glu Tyr Ser Trp Thr Gly Ala Thr Lys Tyr His Leu Asn Gly
                500                 505                 510

Arg Asp Ser Leu Val Asn Pro Gly Pro Ala Met Ala Ser His Lys Asp
            515                 520                 525

Asn Glu Glu Lys Phe Phe Pro Gln Ser Gly Val Leu Ile Phe Gly Lys
            530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                    565                 570                 575

Gly Ser Val Ser Thr Asn Leu Gln Arg Gly Asn Arg Gln Ala Ala Thr
                580                 585                 590

Ala Asp Val Asn Thr Gln Gly Val Leu Pro Gly Met Val Trp Gln Asp
            595                 600                 605

Arg Asp Val Tyr Leu Gln Gly Pro Ile Trp Ala Lys Ile Pro His Thr
            610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                    645                 650                 655

Pro Ser Thr Thr Phe Ser Ala Ala Lys Phe Ala Ser Phe Ile Thr Gln
                660                 665                 670

Tyr Ser Thr Gly Gln Val Ser Val Glu Ile Glu Trp Glu Leu Gln Lys
            675                 680                 685

Glu Asn Ser Lys Arg Trp Asn Pro Glu Ile Gln Tyr Thr Ser Asn Tyr
            690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                    725                 730                 735

<210> SEQ ID NO 18
<211> LENGTH: 4
<212> TYPE: PRT
<213> ORGANISM: Unknown
<220> FEATURE:
<223> OTHER INFORMATION: chemically synthesized heparin binding domain

<400> SEQUENCE: 18

Arg Gly Asn Arg
1

<210> SEQ ID NO 19
<211> LENGTH: 4
<212> TYPE: PRT
<213> ORGANISM: Unknown
<220> FEATURE:
<223> OTHER INFORMATION: chemically synthesized heparin binding domain
```

```
<400> SEQUENCE: 19

Ser Gly Asn Thr
1
```